(12) United States Patent
Marisi

(10) Patent No.: US 7,331,949 B2
(45) Date of Patent: Feb. 19, 2008

(54) URINARY CATHETER WITH CHECK VALVE

(76) Inventor: Margaret Grahn Marisi, 45 Red Cedar Dr., Cranston, RI (US) 02920

( * ) Notice: Subject to any disclaimer, the term of this patent is extended or adjusted under 35 U.S.C. 154(b) by 450 days.

(21) Appl. No.: 10/248,888

(22) Filed: Feb. 27, 2003

(65) Prior Publication Data

US 2004/0172009 A1    Sep. 2, 2004

(51) Int. Cl.
*A61M 27/00* (2006.01)
*A61M 1/00* (2006.01)
*A61M 39/00* (2006.01)

(52) U.S. Cl. .............. 604/544; 604/323; 604/326; 604/533

(58) Field of Classification Search .......... 604/276, 604/523, 532–535, 538, 284, 544, 323, 326, 604/907, 912, 915, 96.01, 247, 241; 137/247.21, 137/511, 515, 521
See application file for complete search history.

(56) References Cited

U.S. PATENT DOCUMENTS

| 2,352,642 | A | * | 7/1944 | Langdon ............... 137/849 |
| 2,662,724 | A | * | 12/1953 | Kravagna .............. 137/847 |
| 3,118,468 | A | * | 1/1964 | Bochan ................ 137/846 |
| 3,463,159 | A | * | 8/1969 | Heimlich .............. 604/247 |
| 3,601,125 | A | * | 8/1971 | Moss ................. 604/347 |
| 3,961,529 | A | | 6/1976 | Hanifl ................ 73/219 |
| 3,965,910 | A | | 6/1976 | Fischer ............... 128/349 R |
| 3,967,645 | A | * | 7/1976 | Gregory ............... 137/846 |
| 3,968,925 | A | | 7/1976 | Johnston et al. ........ 229/62.5 |
| 4,227,533 | A | * | 10/1980 | Godfrey ............... 604/247 |
| D269,633 | S | * | 7/1983 | Willinger et al. ........ D23/237 |
| 4,533,354 | A | | 8/1985 | Jensen ................ 604/323 |
| 4,629,159 | A | * | 12/1986 | Wellenstam ............ 251/149.6 |
| 4,828,554 | A | | 5/1989 | Griffin ................ 604/350 |
| 4,932,938 | A | * | 6/1990 | Goldberg et al. ........ 604/99.04 |
| 4,946,449 | A | * | 8/1990 | Davis, Jr. .............. 604/256 |
| 4,946,451 | A | * | 8/1990 | Cianci ................ 604/323 |
| 5,041,092 | A | * | 8/1991 | Barwick ............... 604/104 |
| 5,088,984 | A | * | 2/1992 | Fields ................ 604/167.02 |
| 5,100,395 | A | * | 3/1992 | Rosenberg ............. 604/284 |
| 5,171,305 | A | * | 12/1992 | Schickling et al. ........ 604/271 |
| 5,181,913 | A | | 1/1993 | Erlich ................ 604/263 |
| 5,224,938 | A | * | 7/1993 | Fenton, Jr. ............ 604/247 |

(Continued)

*Primary Examiner*—Tatyana Zalukaeva
*Assistant Examiner*—Michael G Bogart
(74) *Attorney, Agent, or Firm*—Barlow, Josephs & Holmes, Ltd.

(57) ABSTRACT

The present invention provides a novel construction for a catheter that includes backflow prevention in the form of a check valve, which keeps the flow of drained fluid material from reentering the patient. The catheter construction of the present invention provides a standard single or multiple lumen tube assembly that extends rearwardly from the insertion end of the catheter to the contact end wherein on the discharge lumen a one way check valve is provided. It is an important feature of the present invention that the check valve is provided as close to the terminal end of the contact end as possible without interfering with the necessary accessory attachment that is typically made thereto. Further, an interlock mechanism may be provided at the terminal end of the catheter for connecting accessories in a positive locking manner. The combination of the valve and the interlock mechanism provides a notable safety and performance improvement that has been previously unknown in the prior art.

17 Claims, 2 Drawing Sheets

U.S. PATENT DOCUMENTS

| | | | |
|---|---|---|---|
| 5,269,755 A * | 12/1993 | Bodicky | 604/523 |
| 5,269,770 A * | 12/1993 | Conway et al. | 604/265 |
| 5,300,049 A | 4/1994 | Hogan | 604/317 |
| 5,306,226 A * | 4/1994 | Salama | 600/29 |
| 5,405,336 A * | 4/1995 | Austin et al. | 604/534 |
| 5,413,599 A * | 5/1995 | Imachi et al. | 623/1.24 |
| 5,496,300 A | 3/1996 | Hirsch et al. | 604/327 |
| 5,613,663 A | 3/1997 | Schmidt et al. | 251/149.2 |
| 5,647,843 A | 7/1997 | Mesrobian et al. | 604/8 |
| 5,660,205 A * | 8/1997 | Epstein | 137/512.15 |
| 5,688,239 A * | 11/1997 | Walker | 604/96.01 |
| 5,707,357 A * | 1/1998 | Mikhail et al. | 604/167.03 |
| 5,924,452 A * | 7/1999 | Szpara et al. | 137/846 |
| 6,007,521 A | 12/1999 | Bidwell et al. | 604/264 |
| 6,090,069 A * | 7/2000 | Walker | 604/102.03 |
| 6,203,321 B1 * | 3/2001 | Helmer et al. | 433/95 |
| 6,248,092 B1 * | 6/2001 | Miraki et al. | 604/96.01 |
| 6,379,372 B1 * | 4/2002 | Dehdashtian et al. | 606/192 |
| 6,508,268 B1 * | 1/2003 | Kouketsu | 137/488 |
| 6,582,395 B1 * | 6/2003 | Burkett et al. | 604/96.01 |
| 6,682,503 B1 * | 1/2004 | Fariss et al. | 604/34 |
| 2001/0049490 A1 * | 12/2001 | Slanda et al. | 604/95.04 |

* cited by examiner

URINARY CATHETER WITH CHECK VALVE

BACKGROUND OF INVENTION

The instant invention relates generally to novel construction for a urinary catheter device. More specifically, the present invention relates to a urinary catheter device that includes a backflow prevention valve that is located in the catheter tube at a point outside the patient's body, providing improved construction and a safer location relative to the prior art devices.

Catheters and other devices for use in the draining of accumulated fluids from the human body or injecting fluids into the body have been widely used in the medical field for a long period of time. In particular, with reference to catheters, there are numerous constructions and designs, each of which is particularly adapted to be inserted into a particularly designated body cavity. For example, a urethral catheter is designed to drain accumulated urine secretions from the bladder. A ventricular catheter is adapted to drain excess cerebrospinal fluid from the brain. A peritoneal catheter is used to drain fluid from the peritoneum; as in kidney dialysis. An enema catheter is used to introduce fluid into the gastrointestinal tract.

All of the above-mentioned types of catheters, as well as others too numerous to enumerate, all have certain design features in common. A typical catheter is formed of hollow, flexible tubing. The tubing is typically comprised of a silicone elastomer such as silicone rubber, a substance which is soft and non-irritating to body tissues. A typical catheter will have a body contact that is designed for insertion into the body and a non-body contact end. One or more inlets are formed proximal to the body contact end. Corresponding outlets will be formed adjacent the non-body contact end, and frequently will be the non-body contact end itself. Catheters designed for different purposes may additionally comprise other structures, but the ones enumerated are generally common to all catheters. Also, the dimensions of the catheter may vary greatly and will be adapted to the purpose for which it is intended. For example, a catheter adapted as a urinary catheter may typically have an outside diameter in the range of 3-8 millimeters. In contrast, a ventricular catheter will have a much smaller diameter.

No matter the particular type, most catheters are used in a similar manner. One end of the catheter is inserted into the body cavity containing the fluid that needs to be drained. The catheter may be inserted directly through a body orifice, such as is the usual case with urethral catheters, or a special opening may have to be made. For example, an opening may have to be made into a vein and the catheter threaded through the vein until it reaches the target body cavity, such as is the case with ventricular catheters. After the catheter is inserted, some means of collecting the fluid must be attached to the non-body contact end. Sometimes, as for ventricular catheters, the catheter will remain entirely within the body and the excess fluid drained will be absorbed by another area of the body. More commonly, however, the excess fluid will simply be collected in a bag or bottle and discarded. The catheter may be left in place for long periods, or the excess body fluid may be drained quickly and the catheter removed after only a short period of insertion.

Further, the structure of catheters may vary relative to the number of simultaneous functions they are designed to perform. Catheters that include one, two or three separate longitudinal passageways, referred to as lumens, are available. Each of these multiple lumen catheters all include a primary lumen that serves as a drainage passageway. A second lumen is provided as a passageway by which to inject air that inflates a balloon on the inserted end of the catheter, thereby retaining the catheter in the patient. Finally, a third lumen may be provided as a means for injecting irrigation water into the cavity for cleansing purposes.

Irrespective of what type of catheter is used, how long it remains in place, or what type of body fluid it is used to drain, all catheters are designed for the single purpose of allowing fluid to drain out of the body cavity into which they are inserted. The difficulty is that as described above, the catheter tube is connected at the outflow end to a collection container. If the catheter remains in place for a period of time, the possibility exists that, should the collection container be crushed or raised above the level of the body cavity being drained, the drained fluid may flow in reverse and reenter the cavity from which it was drained. This is of particular concern in cases where the catheter may be inserted for long periods for constant cavity drainage. In these cases, the drained fluid may remain in the drainage container for several hours allowing the growth of harmful bacteria. Should this fluid be reintroduced to the body cavity serious or even deadly infections could result.

While one prior art catheter disclosed a one-way check valve in the drainage lumen, the valve was located proximal to the insertion end of the catheter. The placement and design of the valve were formulated primarily to retain any fluid that may be within the catheter during withdrawal and disposal. In this manner, the valve prevented fluid from flowing out of the withdrawn catheter onto the floor or more importantly onto the medical professional handling the catheter. However, this valve design is only appropriate for the stated function and several drawbacks with respect to the need identified for the present invention. First, because of the size and location of the valve, in the narrowest diameter of the catheter, the passageway becomes very susceptible to blockage. Second, the valve is located within the patient allowing the potential of drained material for flowing into the patient. Finally, if this valve configuration is used in a double or single lumen design, the catheter cannot be used of irrigation because the valve would block the flow of injected irrigation fluid.

There is therefore a need for a new catheter design that provides for a backflow prevention means that does not allow the flow of drained material to re-enter the body of the patient while also providing a positively locking assembly that further facilitates the delivery of irrigation to the patient should the need arise.

SUMMARY OF INVENTION

In this regard, the present invention provides for a novel construction for a catheter that provides backflow prevention in the form of a check valve that keeps the flow of drained fluid material from reentering the patient. The catheter construction of the present invention provides a standard single or multiple lumen tube assembly that extends rearwardly from the insertion end of the catheter to the contact end wherein on the discharge lumen a one way check valve is provided. It is an important feature of the present invention that the check valve is provided as close to the terminal end of the contact end as possible without interfering with the necessary accessory attachment that is typically made thereto. The check valve is preferably formed as a flap of the same material from which the catheter is formed. The flap is located in the contact end of the catheter at the point where the lumen tube of the catheter begins to flare outwardly to facilitate connections thereto. Placing the valve in this location provides several important advantages over the prior art. First, in this location, the flap of valve material can form a positive seal preventing any back flow of fluid because it is placed in a portion of the lumen tube that tapers inwardly, any backflow would force the flap into the tapered lumen bore causing a positive sealing effect. This effect may be enhances by further providing a seat structure around the interior of the bore against which the flap would come to rest in a backflow condition.

The second advantage provided by placing the valve in this particular position is that it is located physically outside the patient body when the catheter is placed in the operable position. In this manner, the catheter construction insures that not only will the backflow of drained fluid be prevented, but backflow along the entire length of the entire catheter is also prevented in contrast to the devices of the prior art. Another advantage of the present invention is that when employed in a single lumen or double lumen catheter construction, the valve is located at a point well outside the body of the patient. In this manner, a second entry port into the drainage lumen at a point upstream from the valve may be provided if desired to allow irrigation through the catheter as has been previously unknown in the art. With the prior art devices of this type, the only way to facilitate irrigation is through the use of a triple lumen catheter. This is because in the prior art the valve was located at the insertion end of the catheter, well within the body of the patient, where it would be impossible to introduce an additional entry port upstream from the check valve.

Finally, since the valve of the present invention is located in a section of the lumen where the cross sectional area is larger, it is less likely to become clogged by for example, crystals that may be suspended in the patient's urine.

Accordingly, one of the objects of the present invention is the provision of a novel catheter construction that provides protection against the backflow of drained fluid. Another object of the present invention is the provision of a novel catheter construction that prevents that backflow of drained fluid from reentering the body of the patient being treated. A further object of the present invention is the provision of a catheter construction that can be employed equally with the various types of existing catheter configurations to prevent the backflow of drained fluid while further allowing the use of the central lumen for irrigation if necessary. Yet a further object of the present invention is the provision of a catheter construction that prevents the backflow of drained fluid while including a positive interlocking mechanism for the attachment of accessories such as drainage collection containers.

Other objects, features and advantages of the invention shall become apparent as the description thereof proceeds when considered in connection with the accompanying illustrative drawings.

BRIEF DESCRIPTION OF DRAWINGS

In the drawings which illustrate the best mode presently contemplated for carrying out the present invention.

DETAILED DESCRIPTION

Figure 1:
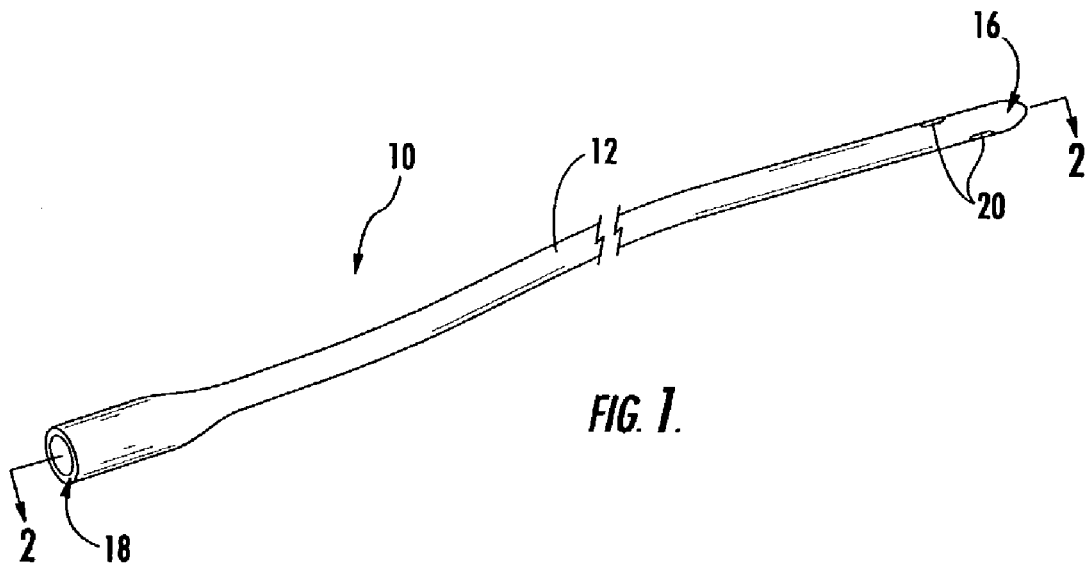
FIG. 1 is a perspective view of a single lumen catheter of the present invention.

Referring now to the drawings, the novel catheter construction of the present invention is illustrated and generally indicated as 10 in FIGS. 1-6. Turning now to FIG. 1, the general shape of the catheter 10 of the present invention has a long tubular body 12 that includes at least one hollow passageway 14 therein and is provided with an inlet end 16 and an outlet end 18. Typically, the entire catheter 10 will be formed from a single elastomeric material such as silicone or a natural latex rubber. The inlet end 16 is formed as a narrow portion of the elongated tube 12 with a rounded or slightly tapered end to facilitate insertion into a body cavity. For example, in the case of the present invention the end is rounded to allow insertion through the external urethral opening and into the bladder. At least one opening 20 is provided at the inlet end 16 of the catheter 10 to allow fluid from the body cavity to enter the hollow passageway 14 on the interior of the catheter 10. The hollow passageway 14 connects on the interior of the catheter 10 from the inlet end 16 to the outlet end 18. The outlet end 18 has a slightly flared profile to allow a further assembly to be attached to the outlet end 18 thereof for collection and disposal of the drained fluid.

Figure 2:
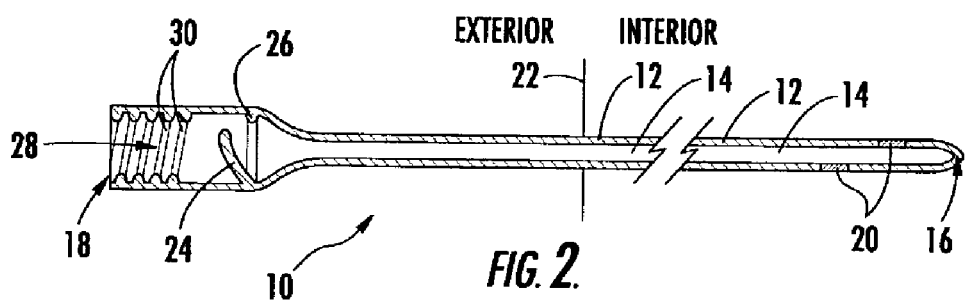
FIG. 2 is a cross-sectional view thereof taken along line 2-2 of FIG. 1.

Turning to FIG. 2, a cross-sectional view of the catheter 10 of the present invention is shown to illustrate the novel features. As was described above, the catheter 10 has a long tubular body 12 with an inlet 16 and outlet end 18 and a hollow passageway 14 extending therebetween. Inlet holes 20 are shown that allow fluid to enter the hollow passageway 14 thereby evacuating the body cavity into which the catheter 10 is inserted. A demarcation line 22 is shown in the figure to illustrate the portion of the catheter 10 that is inserted into the human body and the portion that remains entirely outside the body. As can be seen, the hollow passageway 14 extends throughout the interior length of the catheter 10 to the outlet end 18. The outlet end 18 of the catheter 10 has a flared shape to allow the attachment of an additional apparatus (not shown) such as tubing and a collection bag wherein the fluid that drains through the hollow interior passageway 14 of the catheter 10 is collected for disposal and/or testing. When draining fluid from a human body cavity in this manner, it is important to insure a one-way flow of the drained fluid. Often the fluid that is being drained may contain infectious or diseased materials that could severely harm the patient if reintroduced after being drained and exposed to air for a period of time. For example, in the traditional prior art drainage assembly, if a drainage bag attached to a catheter were to be raised above the level of the inlet end of the catheter or if the drainage bag were to be squeezed, the collected fluid would be allowed to flow in a reverse direction, reintroducing it to the body cavity being drained. The present invention provides a valve to prevent this reverse flow condition from occurring.

On the interior of the hollow passageway 14 in the drainage portion of the catheter 10, a valve flap 24 is provided that allows fluid to pass freely in one direction only, namely from the inlet end 16 to the outlet end 18. Should fluid pressure build on the outlet end 18 of the catheter 10 and attempt to flow in a reverse direction, the check valve 24 will close, preventing the fluid from reentering the catheter passageway 14. While not a critical element of the present invention, a further ridge 26 may be provided around the interior wall of the catheter 10 to create a seat against which the check valve 24 can be firmly sealed increasing the quality of the seal provided. All of the components of the catheter 10 and check valve 24 will typically be formed from a single material as an integrated assembly. While the check valve 24 is shown here as a flapper type valve, it can be appreciated that the valve may be of any type valve known in the art such as a clamp valve, a ball valve or a gate valve and still be within the present disclosure.

It is important to note the location of the check valve 24 relative to the overall operation of the present invention. First, in viewing the catheter 10 in its operative relation relative to the interior and exterior of the human body as indicated in FIG. 2, the check valve 24 is located outside the body. This critical element distinguishes the present invention from the prior art. Specifically, since the entire check valve 24 and outlet assembly 18 are located outside the human body, any fluid backflow will be completely prevented from reentering the body. By preventing the flow from reentering the body in this manner, the present invention also prevents the potential for introducing harmful organisms or infectious material into the patient. Further, since the check valve 24 is placed at a point in the catheter 10 where the diameter is slightly larger, it is less likely to become clogged. The likelihood of clogging is also reduced by placing the check valve 24 further down the catheter 10 where the pressure of the out flow is higher and more likely to dislodge potential clogs such as accumulated crystal materials in the patient's urine.

Figure 3:
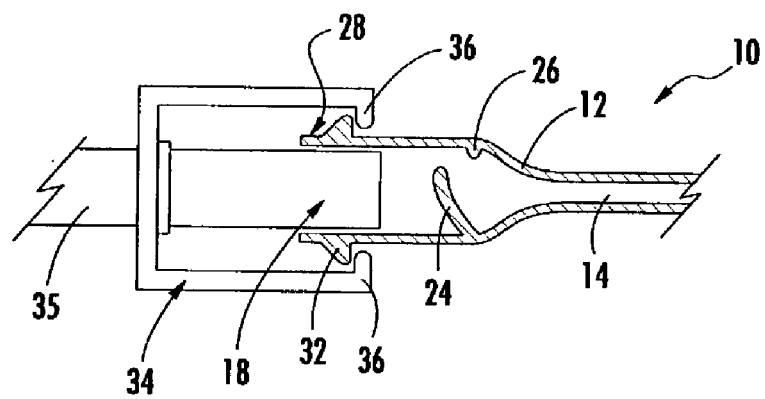
FIG. 3 is a partial cross-sectional view of an alternate embodiment thereof.

Another important feature provided in the present invention is the positive locking assembly 28 provided on the outlet end 18 of the catheter 10. In the preferred embodiment, female threads 30 are provided within the inner surface of the catheter 10 wall. The female threads 30 are provided to engage corresponding male threads (not shown) on any attachments connected thereto, preventing accidental disengagement of the collection assembly from the outlet end 18 of the catheter 10. This is a further safety enhancement that can be contrasted to the catheters of the prior art. Typically, this connection point would simply rely on a frictional engagement to maintain the catheter and collection device in assembled relation. This made the potential for accidental dislodgement of the collection assembly highly likely. Should this dislodgement occur, infectious materials may be spilled or a pathway for infectious material to enter the body may be left open. In FIG. 3 an alternate embodiment for the positive attachment means 28 described herein is shown. In this embodiment, a ridge 32 is provided, which is integrally formed on the exterior of the catheter 10 wall 12. A latching assembly 34 provided on the mating end of the collection device 35 includes hooks 36 that engage the ridge 32 thereby holding the collection device 35 and catheter 10 in mated relation preventing accidental dislodgement.

Figure 4:
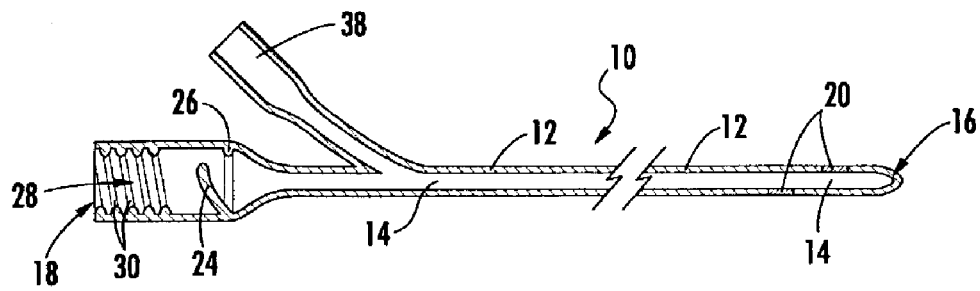
FIG. 4 is a cross-sectional view of a second alternate embodiment thereof.

Turning now to FIG. 4, an alternate embodiment of the present invention is shown that is particularly suited for use as a catheter 10 where the patient's condition may require the introduction of irrigation fluids into the body cavity being evacuated. In this embodiment, a second outlet port 38 is provided in fluid communication with the hollow passageway 14 in the catheter tube 10 at a point upstream from the check valve 24. As can be seen, while it would not be possible to introduce fluid into the catheter 10 via the outlet end 18 because the check valve 24 would prevent its introduction, the additional port 38 allows the introduction of the desired irrigation fluid. The irrigation fluid is introduced into the second port 38 under pressure from, for example, a syringe. The port 39 is then closed and the irrigation fluid as well as any dislodged material can be allowed to drain through the catheter 10 in a normal fashion through the tube 14, through the check valve 24 and out the outlet assembly 18 into the collection device.

Figure 5:
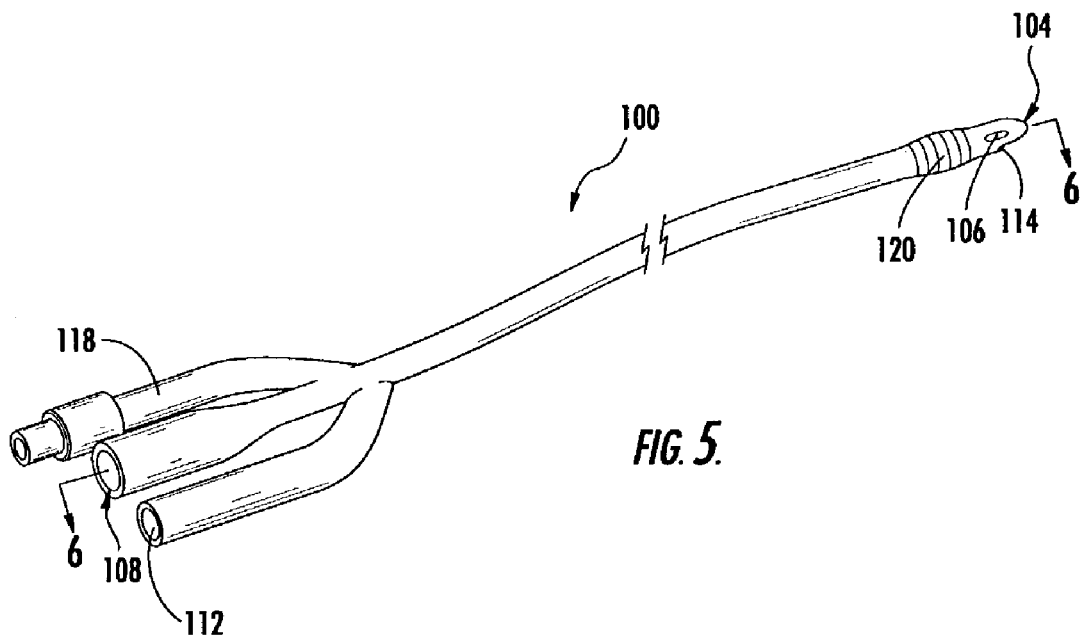
FIG. 5 is a perspective view of a triple lumen catheter of a third alternate embodiment of the present invention.
Figure 6:
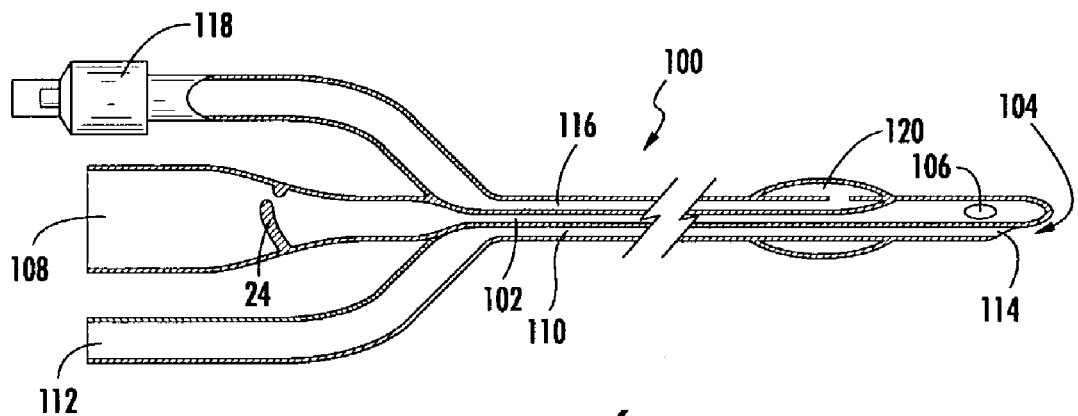
FIG. 6 is a cross-sectional view thereof taken along line 6-6 of FIG. 5.

Finally, turning to FIGS. 5 and 6, another alternate embodiment of the present invention is shown in the form of a triple lumen catheter 100. This catheter 100 is identical in operation to the single lumen catheter 10 described above. The tubular catheter 100 has a hollow passageway 102 on its interior with an inlet end 104 that is inserted into the body cavity of the patient. The inlet end 104 includes ports 106 that allow the fluid in the cavity to enter into the hollow passageway 102 and flow through the catheter 100 to ultimately exit on the outlet end 108 into a collection device. The drainage passageway 102 includes the one-way check valve 24 as described above to prevent the backflow of the drainage material. In addition, however, this embodiment also includes a separate passageway 110 that is included solely for the introduction of irrigation fluid. The passageway 110 has one end 112 for injection of the irrigation fluid and an outlet end 114 proximate to the inlet ports 106 on the insertion end 104 of the catheter 100. The irrigation fluid is thereby introduced to the body cavity and allowed to drain through the drainage passageway 102 in the catheter 100. The third lumen 116 in the catheter 100 is provided as a mechanism by which the catheter 100 is retained in the patient's body cavity for long periods of time. The exterior end 118 of this lumen 116 is designed to allow air to be introduced and retained under pressure. On the interior of the patient the third lumen 116 terminates in an inflatable balloon structure 120 that expands when air pressure is introduced, thereby preventing the catheter 100 from being withdrawn from the patient. This catheter 100 may also include the positive locking assembly on the outlet end 108 as described above.

It can therefore be seen that the present invention provides a novel catheter construction 10 that enhances the safety for both the patient and the user by preventing the potential of the backflow of drained fluids back into the patient through the use of a check valve 24 and preventing the accidental dislodgement of the collection device from the outlet end 18 of the catheter 10. Further, the present invention insures that in a backflow condition no backflow material will reenter the interior of the patient's body at any point. For these reasons, the instant invention is believed to represent a significant advancement in the art, which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

The invention claimed is:

1. A catheter including an integrally formed check valve for the transfer of body fluids comprising:

a tubular catheter having a first end, a second end and at least one hollow passageway within said tubular catheter extending from said first end to said second end, and having at least one inlet disposed proximate said first end and at least one outlet disposed proximate said second end, wherein the interior diameter of said hollow passageway has a tapered transition from a first diameter to a second diameter larger than said first diameter proximate said second end;

a valve seat ridge that is integrally formed as part of a side wall of said tubular catheter downstream from said smaller first lumen at said tapered transition;

a valve flap integrally formed entirely within said hollow passageway in said catheter proximate said tapered transition and said valve seat ridge, said valve seat allowing said valve flap to open in a first direction away from said valve seat and preventing said valve flap from inverting through said valve seat, said valve flap substantially limiting the fluid flow therethrough to a single direction from said first end to said second end while freely and automatically allowing fluid flow in said single direction; and an interlocking means at said second end of said catheter for selectively connecting a collection apparatus thereto.

2. The catheter for the transfer of body fluids of claim 1, said interlocking means further comprising:

a screw thread pattern at said second end of said catheter, said screw thread pattern corresponding to a mating screw thread pattern on said collection apparatus, wherein said screw thread pattern facilitates a positive interlocking connection between said second end of said catheter and said collection apparatus.

3. The catheter for the transfer of body fluids of claim 1, said interlocking means further comprising:

a raised ridge extending around said second end of said catheter, and hooks extending from said collection apparatus, wherein said hooks engage said ridge to facilitate a positive interlocking connection between said second end of said catheter and said collection apparatus.

4. The catheter for the transfer of body fluids of claim 1, wherein said first end is inserted into a human body into a body cavity contained therein to drain fluids contained in said cavity, said second end and said check valve remaining entirely outside said human body.

5. The catheter for the transfer of body fluids of claim 1, wherein said at least one hollow tube is exactly one hollow tube.

6. The catheter for the transfer of body fluids of claim 1, said at least one hollow tube further comprising:

a first hollow tube providing means for transferring body fluids from a body cavity into which said first end of said catheter is inserted;

a second hollow tube providing means for retaining said catheter in said body cavity; and a third hollow tube providing means for introducing irrigation fluid to said body cavity.

7. The catheter for the transfer of body fluids of claim 1 said at least one hollow tube further comprising:

a hollow passageway extending from said first end to said second end and having at least one inlet disposed proximate said first end, a first outlet disposed proximate said second end and a check valve disposed within said hollow passageway in said catheter between said first end and said outlet proximate said second end, said check valve substantially limiting the fluid flow therethrough to a single direction from said first end to said second end;

a second outlet proximate said second end of said catheter between said first end and said second end, said second outlet allowing the introduction of irrigation fluid into said catheter.

8. The catheter for the transfer of body fluids of claim 1 wherein said valve is a check valve.

9. A catheter including an integrally formed check valve for the transfer of body fluids comprising:

a tubular catheter having a first end, a second end and at least one hollow passageway within said tubular catheter extending from said first end to said second end, and having at least one inlet disposed proximate said first end and at least one outlet disposed proximate said second end, wherein the interior diameter of said hollow passageway has a tapered transition from a first diameter to a second diameter larger than said first diameter proximate said second end;

said transition forming a valve seat ridge that is integrally formed as part of a side wall of said tubular catheter downstream from said smaller first lumen at said tapered transition; and a valve flap integrally formed entirely within said hollow passageway in said catheter proximate said tapered transition and said valve seat ridge, said valve seat allowing said valve flap to open in a first direction away from said valve seat and preventing said valve flap from inverting through said valve seat, said valve flap substantially limiting the fluid flow therethrough to a single direction from said first end to said second end while freely and automatically allowing fluid flow in said single direction, wherein said first end of said catheter is inserted into a human body into a body cavity contained therein to drain fluids contained in said cavity, said second end and said check valve remaining entirely outside said human body.

10. The catheter for the transfer of body fluids of claim 9, further comprising:

an interlocking means at said second end of said catheter for selectively connecting a collection apparatus thereto.

11. The catheter for the transfer of body fluids of claim 10, said interlocking means further comprising:

a screw thread pattern at said second end of said catheter, said screw thread pattern corresponding to a mating screw thread pattern on said collection apparatus, wherein said screw thread pattern facilitates a positive interlocking connection between said second end of said catheter and said collection apparatus.

12. The catheter for the transfer of body fluids of claim 10, said interlocking means further comprising:

a raised ridge extending around said second end of said catheter, and hooks extending from said collection apparatus, wherein said hooks engage said ridge to facilitate a positive interlocking connection between said second end of said catheter and said collection apparatus.

13. The catheter for the transfer of body fluids of claim 9, said at least one hollow tube further comprising:

a first hollow tube providing means for transferring body fluids from said body cavity;

a second hollow tube providing means for retaining said catheter in said body cavity; and a third hollow tube providing means for introducing irrigation fluid to said body cavity.

14. The catheter for the transfer of body fluids of claim 9 wherein said valve is a check valve.

15. A triple lumen catheter device for the transfer of body fluids comprising:

a tubular catheter having a first end, a second end;

a first hollow passageway within said tubular catheter extending from said first end to said second end, and having at least one inlet disposed proximate said first end and at least one outlet disposed proximate said second end, wherein the interior diameter of said hollow passageway has a tapered transition from a first diameter to a second diameter larger than said first diameter proximate said second end;

said transition forming a valve seat ridge that is integrally formed as part of a side wall of said tubular catheter downstream from said smaller first lumen at said tapered transition;

a check valve integrally formed within said hollow passageway in the catheter proximate said tapered transition and said valve seat ridge, said valve seat allowing said valve to open in a first direction away from said valve seat and preventing said valve from inverting through said valve seat, said check valve substantially limiting the fluid flow therethrough to a single direction from said first end to said second end while freely and automatically allowing fluid flow in said single direction, and an interlocking means at said outlet for selectively connecting a collection apparatus thereto;

a second hollow tube providing means for retaining said catheter in said body cavity; and a third hollow tube providing means for introducing irrigation fluid to said body cavity, wherein said first end of said catheter is inserted into a human body into a body cavity contained therein to drain fluids contained in said cavity, said second end and said check valve remaining entirely outside said human body.

16. A triple lumen catheter device for the transfer of body fluids of claim 15, said interlocking means further comprising:

a screw thread pattern at said second end of said catheter, said screw thread pattern corresponding to a mating screw thread pattern on said collection apparatus, wherein said screw thread pattern facilitates a positive interlocking connection between said second end of said catheter and said collection apparatus.

17. A triple lumen catheter device for the transfer of body fluids of claim 15 said interlocking means further comprising:

a raised ridge extending around said second end of said catheter, and hooks extending from said collection apparatus, wherein said hooks engage said ridge to facilitate a positive interlocking connection between said second end of said catheter and said collection apparatus.

\* \* \* \* \*